United States Patent
Fei et al.

(10) Patent No.: US 10,299,998 B2
(45) Date of Patent: May 28, 2019

(54) SINGLE PHASE WHITENING DENTIFRICE WITH HIGH PURITY METAPHOSPHATE ABRASIVE

(71) Applicant: Colgate-Palmolive Company, New York, NY (US)

(72) Inventors: Lin Fei, Kendall Park, NJ (US); Suman Chopra, Monroe, NJ (US); Prakasarao Mandadi, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/352,669

(22) Filed: Nov. 16, 2016

(65) Prior Publication Data

US 2017/0143599 A1   May 25, 2017

Related U.S. Application Data

(60) Provisional application No. 62/258,313, filed on Nov. 20, 2015.

(51) Int. Cl.

| | | |
|---|---|---|
| *A61K 8/19* | (2006.01) | |
| *A61K 8/22* | (2006.01) | |
| *A61K 8/23* | (2006.01) | |
| *A61K 8/24* | (2006.01) | |
| *A61K 8/46* | (2006.01) | |
| *A61K 8/86* | (2006.01) | |
| *A61Q 11/00* | (2006.01) | |

(52) U.S. Cl.
CPC .............. *A61K 8/24* (2013.01); *A61K 8/19* (2013.01); *A61K 8/22* (2013.01); *A61K 8/23* (2013.01); *A61K 8/463* (2013.01); *A61K 8/466* (2013.01); *A61K 8/86* (2013.01); *A61Q 11/00* (2013.01); *A61K 2800/28* (2013.01); *A61K 2800/31* (2013.01)

(58) Field of Classification Search
CPC ........................................................ A61K 8/18
USPC ............................................................ 424/42
See application file for complete search history.

(56) References Cited

U.S. PATENT DOCUMENTS

| | | | |
|---|---|---|---|
| 3,935,306 A | 1/1976 | Roberts et al. | |
| 4,272,513 A | 6/1981 | Gaffar | |
| 8,591,868 B2 | 11/2013 | Chopra et al. | |
| 2012/0282192 A1* | 11/2012 | Miller | A61K 8/22 424/52 |
| 2014/0348760 A1 | 11/2014 | Chopra et al. | |
| 2015/0305843 A1 | 10/2015 | Maloney et al. | |
| 2015/0320665 A1 | 11/2015 | Fei et al. | |

FOREIGN PATENT DOCUMENTS

| | | |
|---|---|---|
| CH | 539432 | 7/1973 |
| KR | 910002095 | 12/1988 |

OTHER PUBLICATIONS

Phillips et al., "Additional Studies on the Effect of Fluorides on the Hardness of Enamel." The Journal of the American Dental Association, May 1950: vol. 40, No. 5; pp. 513-519.*
International Search Report and Written Opinion from the International Searching Authority in International Application No. PCT/US2016/062142, dated Feb. 13, 2017.

* cited by examiner

*Primary Examiner* — Walter E Webb

(57) ABSTRACT

Provided is a single phase oral care composition having a whitening agent; a first abrasive selected from calcium pyrophosphate, calcium carbonate, and dicalcium phosphate; a second abrasive that may include sodium metaphosphate; an anticalculus agent; and a substantially anhydrous carrier that may include an ethylene oxide/propylene oxide copolymer. In the composition, a wt % of the second abrasive is equal to or greater than a wt % of the first abrasive.

11 Claims, No Drawings

SINGLE PHASE WHITENING DENTIFRICE WITH HIGH PURITY METAPHOSPHATE ABRASIVE

CROSS-REFERENCE TO RELATED PATENT APPLICATIONS

This application claims the benefit of priority to U.S. Provisional Patent Application Ser. No. 62/258,313 filed Nov. 20, 2015, the entireties of which are incorporated herein by reference.

BACKGROUND

Disclosed herein are novel compositions, such as oral care compositions, that include metaphosphate abrasive.

Many individuals desire a "bright" smile and white teeth, and consider dull and stained teeth cosmetically unattractive. Unfortunately, without preventive or remedial measures, stained teeth are almost inevitable due to the absorbent nature of dental material. Everyday activities such as smoking or other oral use of tobacco products, and eating, chewing or drinking certain foods and beverages (in particular coffee, tea and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

There are a variety of compositions described in the art for preventing or treating the discoloration of teeth. In particular, to combat staining and brighten or restore the natural enamel color, a variety of products containing bleaching materials are commercially available for professional and consumer use. The materials most commonly used in teeth whitening today are peroxides. Peroxides are generally deemed safe from a physiological standpoint, and can be effective to whiten teeth.

Professional dental treatments frequently include a tooth surface preparation such as acid etching followed by the application of highly concentrated bleaching solutions (e.g., up to 37% hydrogen peroxide) and/or the application of heat or light. These procedures provide rapid results, but are expensive, and often require several trips to the dentist. Alternatively, at-home bleaching systems can be used. These systems have gained significant popularity in the past decade because of reduced cost, and increased convenience. Instead of time consuming and frequent trips to the dentist, the tooth whitener is purchased at a consumer retail store and may be easily integrated into the daily hygiene program. At-home treatment methods include whitening strips, abrasive toothpastes, and toothpastes that contain peroxides. These peroxide toothpastes require the use of a dual chamber system that separates the peroxide from other ingredients. If the contents of the two chambers are mixed prematurely, the oxidation activity and whitening benefits are lost. To keep peroxide components of the toothpastes stable, non-aqueous liquid carrier and peroxide friendly abrasives, such as calcium pyrophosphate have previously been used. However, changes in the type of liquid carrier have been nearly fully exploited and although calcium pyrophosphate is more stable as compared to, for example, silica and calcium carbonate, such abrasives still may contain hundreds of parts-per-million (ppm) of transition metals which act as catalysts for peroxide decomposition. Accordingly, the wt % of peroxide in the formulation must be kept considerably lower than the professional dental treatments and so whitening effect is limited.

It would be desirable to provide a whitening oral care composition which promotes consumer compliance and utilizes a single chamber or tube to deliver sufficient amounts of whitening ingredients and other oral care actives without adverse reaction between the ingredients.

BRIEF SUMMARY

In an embodiment, there is a single phase oral care composition. The composition includes a whitening agent; a first abrasive selected from the group consisting of calcium pyrophosphate, calcium carbonate, and dicalcium phosphate; a second abrasive comprising sodium metaphosphate; an anticalculus agent; and a substantially anhydrous carrier comprising an ethylene oxide/propylene oxide copolymer, wherein a wt % of the second abrasive is equal to or greater than a wt % of the first abrasive.

In at least one additional embodiment, there is a single phase oral care composition. The composition includes a peroxide whitening agent; an abrasive comprising sodium metaphosphate; an anticalculus agent; and a substantially anhydrous carrier comprising an ethylene oxide/propylene oxide copolymer, wherein the composition does not comprise calcium pyrophosphate.

In at least one additional embodiment there is a method of making a single phase oral care composition. The method can include mixing together a whitening agent, an abrasive, an anticalculus agent and a substantially anhydrous carrier to form a composition, wherein the abrasive comprises sodium metaphosphate, wherein the carrier comprises an ethylene oxide/propylene oxide copolymer, and wherein the composition does not comprise calcium pyrophosphate.

In at least one additional embodiment there are methods of whitening the tooth surfaces by contacting the surface with the composition.

In particular embodiments, the present disclosure provides:

1.1 A single phase oral care composition, comprising:
  (a) a whitening agent;
  (b) a first abrasive wherein the first abrasive is selected from the group consisting of calcium pyrophosphate; calcium carbonate; and dicalcium phosphate;
  (c) a second abrasive comprising sodium metaphosphate;
  (d) an anticalculus agent; and
  (e) a substantially anhydrous carrier comprising an ethylene oxide/propylene oxide copolymer,
  wherein a wt % of the second abrasive is equal to or greater than a wt % of the first abrasive 1.2 Composition 1.1, wherein the whitening agent is a solid whitening agent selected from peroxides, metal chlorites, and persulfates.

1.3 Composition 1.1 or 1.2, wherein the whitening agent is a peroxide selected from hydroperoxides, hydrogen peroxide, peroxides of alkali and alkaline earth metals, organic peroxy compounds, peroxy acids, pharmaceutically-acceptable salts thereof, and mixtures thereof.

1.4 Any preceding Composition, wherein the whitening agent is metal chlorite selected from calcium chlorite, barium chlorite, magnesium chlorite, lithium chlorite, sodium chlorite, potassium chlorite and mixtures thereof.

1.5 Any preceding Composition, wherein the whitening agent is a peroxide bound to a polymer.

1.6 Any preceding Composition, wherein the first abrasive comprises calcium carbonate.
1.7 Any preceding Composition, wherein the wt % of the first abrasive is less than or equal to about 15 wt %.
1.8 Any preceding Composition, wherein the wt % of the first abrasive is less than or equal to about 7 wt %.
1.9 Any preceding Composition, wherein the whitening agent comprises hydrogen peroxide.
1.10 Any preceding Composition, wherein the whitening agent comprises about 0.05 wt % to about 6 wt % of peroxide.
1.11 Any preceding Composition, wherein the anticalculus agent comprises an agent selected from: a polyphosphate; a hexametaphosphate salt; a polyolefin sulfonate; and a combination of two or more thereof
1.12 Any preceding Composition, wherein the carrier has a total water content of less than about 4%, by weight.
1.13 Any preceding Composition, wherein the composition is a dentifrice.
1.14 Any preceding Composition, wherein the composition further comprises sodium lauryl sulfate and a fluoride source.
1.15 A single phase oral care composition, comprising:
 (a) a whitening agent;
 (b) an abrasive comprising sodium metaphosphate;
 (c) an anticalculus agent; and
 (d) a substantially anhydrous carrier comprising an ethylene oxide/propylene oxide copolymer,
 wherein the composition does not comprise calcium pyrophosphate.
1.16 Any preceding Composition, wherein the whitening agent comprises hydrogen peroxide.
1.17 Any preceding Composition, wherein the whitening agent comprises about 0.05 wt % to about 6 wt % of peroxide.
1.18 Any preceding Composition, wherein the anticalculus agent comprises an agent selected from: a polyphosphate; a hexametaphosphate salt; a polyolefin sulfonate; and a combination of two or more thereof.
1.19 Any preceding Composition, wherein the carrier has a total water content of less than about 4%, by weight.
1.20 Any preceding Composition, wherein the composition is a dentifrice.
1.21 Any preceding Composition, wherein the composition further comprises sodium lauryl sulfate and a fluoride source.

In another aspect, the present disclosure provides a method (Method 1) of making a single phase oral care composition, comprising mixing together a whitening agent, an abrasive, an anticalculus agent and a substantially anhydrous carrier to form a composition, wherein the abrasive comprises sodium metaphosphate, wherein the carrier comprises an ethylene oxide/propylene oxide copolymer, and wherein the composition does not comprise calcium pyrophosphate. In a further embodiment of Method 1 (Method 1.1), the composition further comprises calcium pyrophosphate. In a further embodiment of Method 1 or 1.1, the composition does not comprise calcium pyrophosphate.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Disclosed herein are single phase whitening oral care compositions, comprising a whitening agent; one or more of an abrasive; and a substantially anhydrous orally acceptable carrier. In various embodiments, the substantially anhydrous orally acceptable carrier and the particular peroxides employed allow for a shelf-stable single tube oral care composition where the peroxide and the abrasive(s), may be combined. The oral care composition provides highly efficacious whitening and cleaning.

The single phase oral care composition has a "low water" content, meaning that a total concentration of water, including any free water and all water contained in any ingredients, is less than about 4%, about 7% or less than about 10% water. The selection of the whitening agent in conjunction with the low water carrier provides stabilized delivery of the whitening agent. The whitening activity is maintained for application to the tooth or oral surface and is maintained through storage.

Any whitening agent known or developed in the art may be used. Preferably, the whitening agent includes solid whitening agents and bound whitening agents which are substantially anhydrous oxygen generating compounds. Solid whitening agents useful herein include peroxides, metal chlorites, persulfate. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. Suitable metal chlorites include calcium chlorite, barium chlorite, magnesium chlorite, lithium chlorite, sodium chlorite, and potassium chlorite. The whitening agent may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some embodiments, it may be desirable to use any known whitening agent except sodium percarbonate and/or any of the percarbonate salts.

In an example, the composition includes an amount of whitening agent such that a wt % of the whitening agent comprises about 0.05 wt % to about 6 wt %, for example, about 3 wt % or about 5 wt %.

The compositions of the present invention may include one or more dental abrasive, for example, a combination of dental abrasives known or to be developed in the art. "Abrasive" is as used herein is meant to include materials commonly referred to as "polishing agents" as well.

Any orally acceptable abrasive can be used, but preferably, type, fineness (particle size) and amount of abrasive should be selected so that tooth enamel is not excessively abraded in normal use of the composition. Suitable abrasives include without limitation silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, (3-calcium pyrophosphate, tricalcium phosphate, calcium polymetaphosphate and a sodium metaphosphate such as water insoluble sodium polymetaphosphate, which may be in high-purity form (e.g., less than or equal to 100 ppm transition metal).

Average particle size of an abrasive, if present, is generally about 0.1 to about 30 μm, for example about 1 to about 20 μm or about 5 to about 15 μm. One or more abrasives are present in an abrasive effective total amount, typically about 0.1 wt % to about 40 wt %.

In an example, the abrasive component of the composition comprises a first abrasive and a second abrasive. The first abrasive may be selected from the group consisting of calcium pyrophosphate; calcium carbonate; and dicalcium phosphate; a second abrasive comprising sodium metaphosphate. In an example, the first abrasive comprises calcium pyrophosphate. In an example, the second abrasive comprises sodium metaphosphate.

The first abrasive and the second abrasive may be included in various amounts in the composition. For example, amounts of the first and second abrasive may be selected such that a wt % of the second abrasive may be equal to or greater than a wt % of the first abrasive. The relative amounts of the first abrasive and the second abrasive included in the composition may affect the stability of the whitening agent. Thus, a total wt % of both the first and second abrasives may be provided in an amount of 5 total wt % to about 40 total wt %, for example a total of 15 wt % or 20 wt %. In an example, the wt % of the first abrasive is less than or equal to about 15 wt %, such as less than or equal to about 7 wt %. In an example, the total wt % of both abrasives is from 5 to 30 wt %, or from 10 to 30 wt %, or from 15 to 30 wt %, or from 15 to 25 wt %, or from 20 to 25 wt % or from 15 to 20 wt %. In an example, the wt % of the first abrasive may be substantially 0% such that the abrasive component consists essentially of none of the first abrasive, such as none of the calcium pyrophosphate. In other words, the abrasive component may comprise sodium metaphosphate and the composition may comprise substantially no calcium pyrophosphate.

In various embodiments of the present invention, the oral composition comprises an anticalculus agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The anticalculus agent is present at about 0.1% to about 30%. The oral composition may include a mixture of different anticalculus agents. In one preferred embodiment, tetrasodium pyrophosphate (TSPP) and sodium tripolyphosphate (STPP) are used. The anticalculus agent comprises TSPP at about 1% and STPP at about 7% to about 10%.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions.

The carrier is preferably low water content orally acceptable carrier and may include any known ingredients or additives.

In preferred embodiments of this invention, the oral composition is a dentifrice. Such dentifrices may include a dental tablet, toothpaste (dental cream), tooth powders, or gel, or any other known form known to one of skill in the art.

The substantially anhydrous carrier may also comprise various dentifrice ingredients to adjust the rheology and feel of the composition such as humectants, surface active agents, thickening or gelling agents, etc.

The compositions of the present invention preferably comprise a surface active agent. Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

The compositions of the present invention optionally comprise a thickener. Any orally acceptable thickening agent can be used, including without limitation carbomers, also known as carboxyvinyl polymers, carrageenans, also known as Irish moss and more particularly i-carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

In various preferred embodiments, the carrier may comprise polymers and/or copolymers of polyethylene glycol, of ethylene oxide, of propylene oxide, and of silicone. Such polymers include polyethylene glycol, for example, polyethylene glycol having a molecular weight of 200 to 800 daltons (e.g., PEG 200, PEG 300, PEG 400, or PEG 600). Such polymers also include copolymers of ethylene glycol and propylene glycol. If such copolymers/polymers are used, they may be selected from the commercially available materials PLURACARE® L4370 and PLURACARE® L1220 (available from BASF, Wyandotte, Mich., United States of America). It is preferred that the carrier(s) provide a dentifrice with a viscosity of about 10,000 CPS to about 700,000 CPS, preferably about 30,000 CPS to about 400,000 CPS. In some embodiments, the carrier may comprise an ethylene oxide/propylene oxide block copolymer if the formula (ethylene oxide)x-(propylene oxide)y, wherein x is from 80 to 150 (e.g., from 100-130, or about 118), and wherein y is from 30 to 80 (e.g., from 60-70, or about 66). In some embodiments, the ethylene oxide/propylene oxide block copolymer has the formula (ethylene oxide)x-(propylene oxide)y, wherein x is from 20 to 70 (e.g., from 30-50, or about 38), and wherein y is from 4 to 20 (e.g., from 6-12, or about 8). In some embodiments, the polymers or copolymers have a weight average molecular weight of greater than 5000 daltons, e.g., 8000 to 13,000 daltons, or about 9800 daltons.

As recognized by one of skill in the art, the oral compositions of the present invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention optionally comprise one or more further active material(s), which is operable for the prevention or treatment of a condition or disorder of hard or soft tissue of the oral cavity, the prevention or treatment of a physiological disorder or condition, or to provide a cosmetic benefit.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The compositions of the present invention optionally comprise an antimicrobial (e.g., antibacterial) agent. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3% or about 1 to 3% or about 1 to 2% or about 1% or about 2%. Suitable antimicrobial agents include, but are not limited to, zinc salts (e.g., zinc sulfate, zinc oxide, zinc citrate, zinc lactate, zinc glycerophosphate), stannous salts (e.g., stannous chloride, stannous fluoride), and *magnolia* extract derivatives (i.e., magnolol, honokiol, tetrahydrohonokiol, propyl magnolol, butyl magnolol, and isobutyl magnolol), and any combinations thereof.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a sialagogue or saliva-stimulating agent, an anti-plaque agent, an anti-inflammatory agent, a desensitizing agent.

Methods are provided to whiten an oral surface in a human or animal subject comprising storing in stable form a whitening oral care composition comprising a peroxide whitening agent, one or more of an abrasive, and a substantially anhydrous orally acceptable carrier; and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the one or more of an abrasive, and other ingredients.

In various embodiments, it is preferred that the oral care composition is applied and contacted with the oral surface. The dentifrice, prepared in accordance with the present invention is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The invention is illustrated in the following non-limiting examples.

EXAMPLE 1

Three dentifrice compositions A, B and C, were prepared by mixing the ingredients of Table 1. It is noted that the sodium acid pyrophosphate concentration for composition A was adjusted slightly to bring it to the same pH level as that of composition B.

TABLE 1

|  | A | B | C |
|---|---|---|---|
| Polyethylene glycol 600 | 10.00 | 10.00 | 10.00 |
| Polyethylene glycol/polypropylene glycol 116/66 copolymer | 7.50 | 7.50 | 7.50 |
| Propylene glycol | 43.31 | 43.01 | 43.01 |
| Flavor | 2.25 | 2.25 | 2.25 |
| BHT | 0.03 | 0.03 | 0.03 |
| TSPP | 1.00 | 1.00 | 1.00 |
| Sodium MFP | 0.76 | 0.76 | 0.76 |
| Sodium saccharin | 0.80 | 0.80 | 0.80 |
| Sodium acid pyrophosphate | 0.30 | 0.60 | 0.60 |
| Sucralose | 0.05 | 0.05 | 0.05 |
| Fumed silica | 0.5 | 0.5 | 0.5 |
| Cross-linked PVP-HP | 16.5 | 16.5 | 16.5 |
| Sodium meta phosphate | 15 | — | 7.5 |
| Calcium pyrophosphate | — | 15 | 7.5 |
| Sodium lauryl sulfate | 2 | 2 | 2 |
| Total | 100 | 100 | 100 |

Peroxide stability was monitored through titration after each week of aging. After aging the dentifrice compositions A, B and C for five weeks at approximately 60° C., the peroxide recovery was 74.7%, 28.6% and 56.8%, respectively, of the initially present amount in each composition.

Table 2 shows peroxide concentration for compositions A, B and C through five weeks of aging.

TABLE 2

| Aging time (week) | 0 | 1 | 2 | 3 | 4 | 5 |
|---|---|---|---|---|---|---|
| Dentifrice Composition A | 3.00 | 2.66 | 2.52 | 2.48 | 2.47 | 2.24 |
| Dentifrice Composition B | 3.00 | 2.52 | 2.05 | 1.57 | 1.23 | 0.86 |
| Dentifrice Composition C | 3.00 | 2.84 | 2.59 | 2.20 | 1.87 | 1.67 |

These results clearly show that high purity sodium metaphosphate is significantly more compatible with hydrogen peroxide. Said another way, dentifrice compositions containing sodium metaphosphate and substantially no calcium pyrophosphate degraded significantly less and slower during accelerated aging than in the dentifrice composition containing calcium pyrophosphate.

EXAMPLE 2

Two additional compositions were prepared, Compositions D and E, to test the effect of replacing calcium pyrophosphate abrasive with sodium metaphosphate abrasive in a whitening system based on potassium peroxymonosulfate as the whitening agent. Compositions D and E each comprise about 5 wt % potassium peroxymonosulfate, provided as the commercial triple salt mixture Caroat (a mixture of KHSO5, KHSO4 and K2SO4; net content about 50 wt % active potassium peroxymonosulfate). The formulation of Compositions D and E are shown in Table 3 below:

TABLE 3

| | D | E |
|---|---|---|
| Polyethylene glycol 600 | 6.0 | 6.0 |
| Polyethylene glycol/polypropylene glycol 116/66 copolymer | 10.0 | 10.0 |
| Propylene glycol | 33.11 | 33.11 |
| Flavor | 2.25 | 2.25 |
| BHT | 0.03 | 0.03 |
| TSPP | 12.00 | 12.00 |
| Sodium MFP | 0.76 | 0.76 |
| Sodium saccharin | 0.80 | 0.80 |
| Polyvinyl pyrrolidone | 2.0 | 2.0 |
| Sucralose | 0.05 | 0.05 |
| Fumed silica | 1.0 | 1.0 |
| Caroat (contains 50% Potassium peroxymonosulfate) | 10.0 | 10.0 |
| Sodium meta phosphate | 20 | — |
| Calcium pyrophosphate | — | 20 |
| Sodium lauryl sulfate | 2 | 2 |
| Total | 100 | 100 |

Active oxygen concentration was measured initially and after one month of accelerated aging at 40° C. and a relative humidity of 75%. The results are shown in Table 4 below:

TABLE 4

| | D | E |
|---|---|---|
| Initial | 0.49% | 0.44% |
| Aging (40 C., 1 month, 75% RH) | 0.25% | 0.099% |
| Active Oxygen % reduction | 49.0% | 77.5% |

The results demonstrate that substitution of sodium metaphosphate for calcium pyrophosphate unexpectedly results in significantly improved active oxygen stability. While accelerated aging results in more than three-quarters of the initial activity being lost in a composition with calcium pyrophosphate abrasive, only about half of the initial oxygen activity is lost when sodium metaphosphate abrasive is used.

Taken together, Examples 1 and 2 demonstrate that the use of sodium metaphosphate abrasive in oral whitening compositions achieves significant improvements in oxidizing agent stability and shelf-life for diverse whitening agent species.

What is claimed is:

1. A single phase oral care composition, comprising:
   a whitening agent;
   a first abrasive comprising sodium metaphosphate;
   a second abrasive;
   an anticalculus agent; and
   a substantially anhydrous carrier comprising an ethylene oxide/propylene oxide copolymer,
   wherein a wt % of the second abrasive is equal to or greater than wt % of the first abrasive and wherein the whitening agent is potassium persulfate (potassium peroxymonosulfate).

2. The composition of claim 1, wherein the second abrasive is not calcium pyrophosphate.

3. The composition of claim 1, wherein the anticalculus agent comprises an agent selected from: a polyphosphate; a hexametaphosphate salt; a polyolefin sulfonate; and a combination of two or more thereof.

4. The composition of claim 1, wherein the carrier has a total water content of less than about 4%, by weight.

5. The composition of claim 1, wherein the composition is a dentifrice.

6. The composition of claim 1, wherein the composition further comprises sodium lauryl sulfate and a fluoride source.

7. A single phase oral care composition, comprising:
   a whitening agent;
   a first abrasive comprising sodium metaphosphate;
   fumed silica;
   an anticalculus agent; and
   a substantially anhydrous carrier comprising an ethylene oxide/propylene oxide copolymer,
   wherein a wt % of the fumed silica is less than wt % of the first abrasive and wherein the whitening agent is potassium persulfate (potassium peroxymonosulfate).

8. The composition of claim 7, wherein the anticalculus agent comprises an agent selected from: a polyphosphate; a hexametaphosphate salt; a polyolefin sulfonate; and a combination of two or more thereof.

9. The composition of claim 7, wherein the carrier has a total water content of less than about 4%, by weight.

10. The composition of claim 7, wherein the composition is a dentifrice.

11. The composition of claim 7, wherein the composition further comprises sodium lauryl sulfate and a fluoride source.

* * * * *